United States Patent [19]

Jolly et al.

[11] Patent Number: 4,822,371
[45] Date of Patent: Apr. 18, 1989

[54] REINFORCED ELASTIC SLEEVE FOR USE WITH A LIMB PROSTHETIC DEVICE

[76] Inventors: David F. Jolly, 2250 Holly Hall, Apt. #292, Houston, Tex. 77054; Michael T. Wilson, 3131 Villa La., Missouri City, Tex. 77459

[21] Appl. No.: 6,682

[22] Filed: Jan. 23, 1987

[51] Int. Cl.⁴ ................................................. A61F 2/78
[52] U.S. Cl. ........................................ 623/32; 623/57; 128/80 C; 128/77
[58] Field of Search .................... 623/27, 32, 57, 58, 623/33–37; 128/80 C, 80 F, 80 R, 77

[56] References Cited

U.S. PATENT DOCUMENTS 3,888,244  6/1975  Lebold .................................. 128/77
4,474,573  10/1984  Detty .................................. 128/80 C Primary Examiner—Richard J. Apley
Assistant Examiner—Alan W. Cannon
Attorney, Agent, or Firm—Phillips, Moore, Lempio & Finley

[57] ABSTRACT

The present invention relates to an integral elastic suspension sleeve for use with an artificial limb prosthetic device. Specifically, the invention is an integral flexible elastic support sleeve having two circular ends which encloses and securely grips the residual lower extremity portion of a human being who has had a below the knee (or below the elbow) amputation and also encloses and securely grips the top outer surface of the socket of a shin and foot (or forearm and hand) prosthetic device. The suspension sleeve has a smaller internal cylindrical-like panel which has a fabric surface having a low coefficient of friction. This fabric surface is in contact with the outer intersection line between the prosthetic device and the limb extremity of the human being. This sleeve is at between about 5° and 45° angle, and the described configuration results in improved mobility, decreased dermatological irritation to the wearer and enhances the longevity of the elastic suspension sleeve.

2 Claims, 2 Drawing Sheets

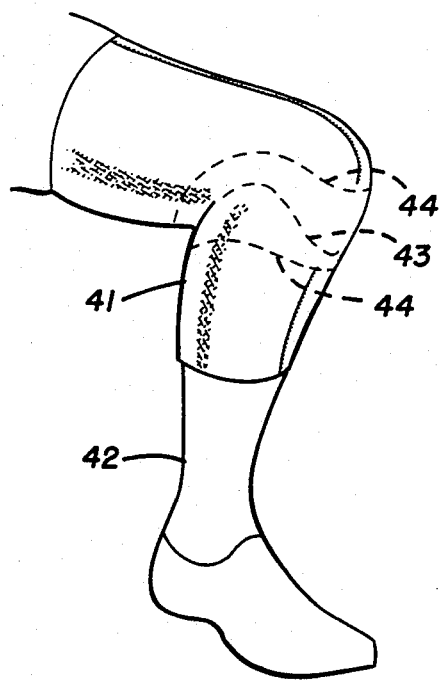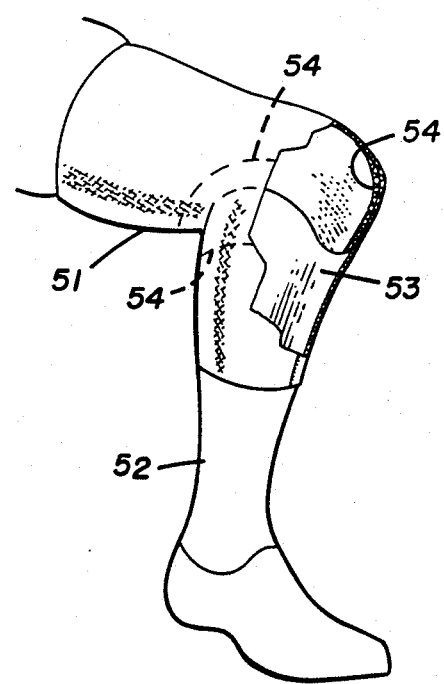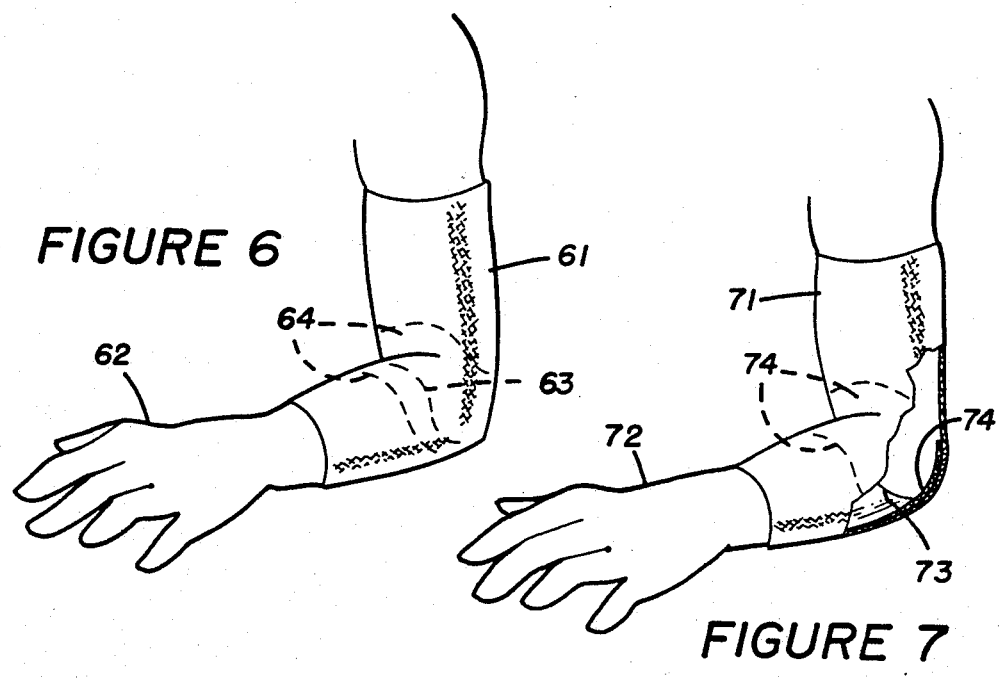
FIGURE 4    FIGURE 5
FIGURE 6    FIGURE 7

REINFORCED ELASTIC SLEEVE FOR USE WITH A LIMB PROSTHETIC DEVICE

BACKGROUND OF THE INVENTION

1. Field of the Invention

The present invention relates to an integral elastic suspension sleeve for use with an artificial shin and foot (below the knee prosthesis) or an artificial hand and forearm (below the elbow). More specifically, the invention discloses an integral flexible elastic support sleeve having two open ends which encloses and securely grips the thigh (or forearm) portion of a human being who has had a below the knee (or below the elbow) amputation and also encloses and securely grips the top of the socket of the limb prosthetic device. The sleeve inherently and by design yields and moves easily in accordance with the movements of the thigh, knee (or forearm and elbow) and the prosthetic device.

2. Description of the Prior Art

Elastic supports for enclosing a body member are known in the art. For instance, Lon R. Hettick discloses in U.S. Pat. No. 4,084,586 a tubular elastic support having a fabric facing bonded to the interior and to the exterior surfaces each having low coefficients of friction and the same stretch rate as the elastic center portion. These tubular supports are useful to assist in the healing of, for instance, a damaged ankle, knee, back, hand, elbow, or the like. Both sides of the tubular support described in the patent have facings with a low coefficient of friction. Therefore, the tubular support, when in place on the human body, does not cling to or gather any clothing of the wearer. Further, because the inner surface has a complete facing, the body member moves easily within the tubular support and the support is easily put on or removed. This type of tubular support moves easily on the surface of the skin and is not air tight.

A. Staros and B. Goralnik in "Lower Limb Prosthetic Systems" in *Atlas of Limb Prosthetics*, published by E. V. Mosby Co. of St. Louis, Mo. in 1981 disclose specific terminology and configurations of sockets and suspension designs.

Other types of suspension for prosthetic devices include the following:

(1) adjustable belts suspended from the shoulders, waist and knee; (2) supracondylar suspension; (3) thigh lacer and metal joints; (4) suction sockets; and the like.

The use of elastic sleeves to provide support for a prosthetic device is known. However, there are no known atmospheric suspension sleeves for use with a prosthetic device which include preflexion or a fabric interliner, i.e., the sleeves are straight and have no fabric on the inner surface covering the intersection line of the surface of the lower extremity and the proximal terminating border of the prosthetic device. The present elastic sleeve therefore tends to "bunch up" in the area in the back of the knee during normal use. Since the nerves and blood vessels behind the knee are susceptible to localized pressure, this bunching can be uncomfortable and potentially tramatizing to the lower extremity of the wearer. Further, without a fabric of some type on the support sleeve at the surface of the intersection of the lower extremity and the socket of the prosthetic device, the suspension sleeve of the art is subject to rapid deterioration through the shearing force that occurs during normal utilization. Further, the absence of a fabric reinforcement panel induces negative pressure and potential edema along the margin of the external edge of the socket sleeve and the tissue interface.

SUMMARY OF THE INVENTION

The present invention relates to an integral elastic supple suspension sleeve formed from a single sheet of material for holding a limb prosthetic device (foot and shin or hand and forearm) securely on the end of the residual limb of a human being having a amputation, which suspension sleeve comprises:

an integral elastic substantially tubular suspension sleeve having two substantially circular open ends, one open end for receiving and securely gripping the thigh and knee (or forearm and hand) portion of the human being, and the other circular end for receiving and securely gripping the outer surface of the socket portion of the prosthetic device;

said integral elastic support sleeve itself comprising:

(i) a laminate flexible cellular polymeric material, having an inner surface with a high coefficient of friction, and an outer surface of the sleeve having an adherent facing fabric having a lower coefficient of friction covering substantially all of the outer surface of the sleeve, and;

(ii) an inner panel consisting essentially of a laminate of cellular polymeric material which is adhered to the inner surface of the sleeve said inner panel having an outer fabric facing having a lower coefficient of friction, which panel is positioned to be in contact with the intersection line of the proximal terminating border (upper surface portion) of the socket of the prosthetic device and the limb extremity surface of the human being.

In another aspect the support sleeve in the above description creates an air-tight chamber to assist in the holding of the prosthetic device securely on the residual limb of a human being.

In another aspect, the present invention relates to an improvement in the wearing of a shin/foot prosthetic device (foot and shin or hand and forearm) by using the support sleeve described herein.

In another aspect, the present invention relates to an integral elastic support sleeve used in combination with a complimentary prosthetic device for the human leg.

In another aspect the present invention relates to a method of producing the support sleeve by first adhering the fabric-cellular polymer laminate to the inside of the sleeve and subsequently sealing all seams at the same time using cement.

In another aspect, the present invention relates to a method of producing the support sleeve by first sealing with cement to produce the overall sleeve, turning the sleeve inside out and bonding the panel (fabric-cellular material/fabric side out) to the surface of the sleeve.

BRIEF DESCRIPTION OF THE FIGURES

FIG. 4 is an isometric view of the exterior of the sleeve in place on the thigh and in conjunction with with the prosthetic device.

FIG. 5 is an isometric cutaway view of the sleeve in place on the thigh and in conjunction with the prosthetic device.

FIG. 6 is an isometric view of the sleeve in place on the forearm in conjunction with an artificial hand prosthetic device.

FIG. 7 is an isometric cutaway view of the of the sleeve in place on the forearm in conjunction with an artificial hand and forearm prosthetic device.

DETAILED DESCRIPTION OF THE INVENTION AND PREFERRED EMBODIMENTS

The present invention relates to an integral elastic atmospheric suspension (AS) support sleeve for use with a below the knee prosthetic device (e.g. artificial leg, artificial foot and shin). Specifically described, the sleeve has a design that allows for a normal range of motion of the wearer at the knee (ususally 0°-160°) while minimizing constriction and restriction especially at the back of the knee. The design further includes a friction-resistant fabric material capable of being bonded to the interior of the elastic (AS) support sleeve in a location consistent with the top rim portion of the socket of the prosthetic device.

Figure 1:
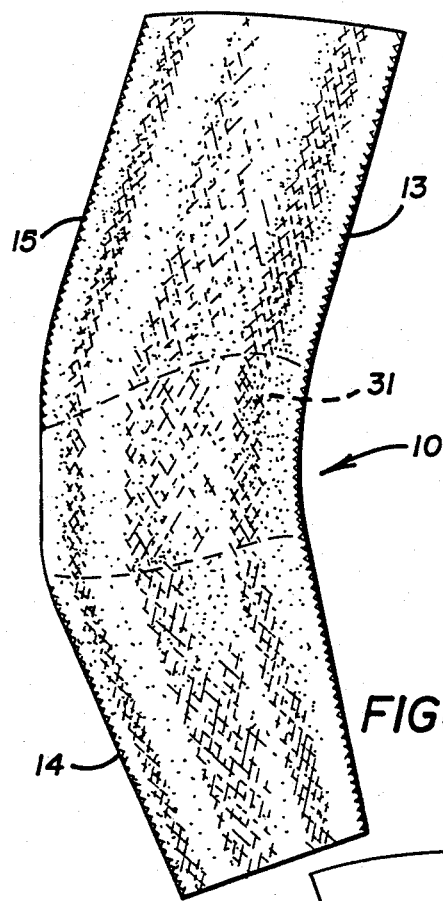
FIG. 1 shows an exterior side view of the flexible support sleeve.
Figure 2:
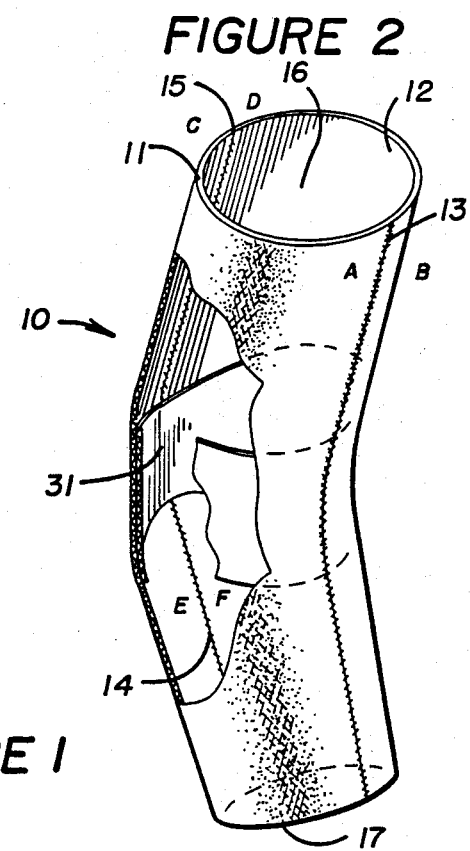
FIG. 2 shows an isometric view of the flexible support sleeve and shows a breakaway view of the inner panel.
Figure 3:
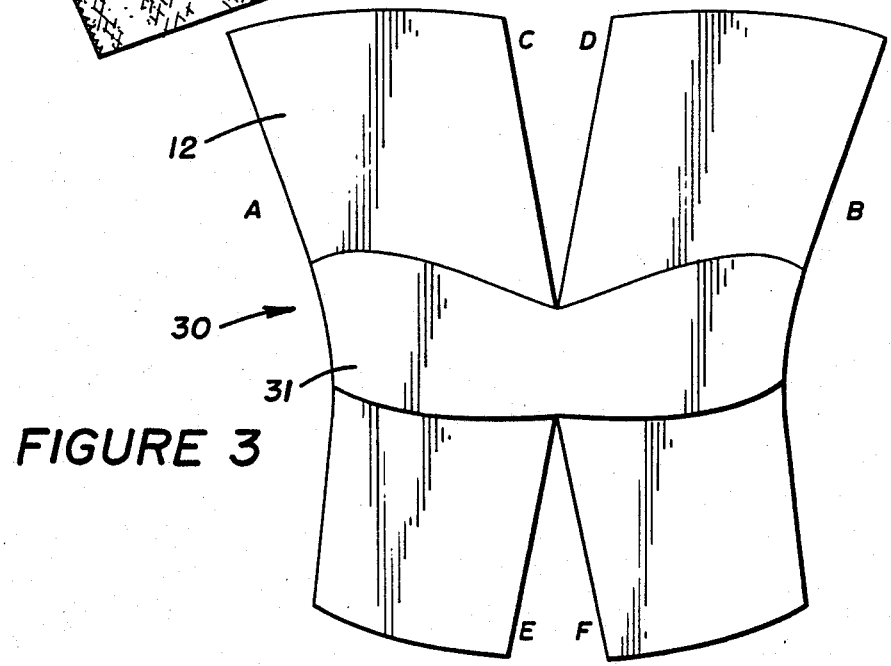
FIG. 3 shows a plan view of a blank sheet useful to form the flexible support sleeve.

Referring now to FIGS. 1 and 2, sleeve 10 is illustrated. The basic sleeve is comprised of one piece of elastic polymeric material. Typically, it is made from a closed cell neoprene type rubber 11 having a smooth surface 12, for instance that which is sold commercially under the trade name NS1 by Rubatex Company of Sausalito, Calif. Any similar closed cell polymeric rubber-like elastomeric material can be used, including rubber material. Blank 30 in Figure 3 is cut roughly in the shape of a large letter 'X'. Smaller panel 31 comprises a laminate of a cellular polymer material and an adherent fabric both having substantially the same elongation as the cellular material 11 of sleeve 10. The fabric facing can be of any suitable natural synthetic fiber or a blend thereof having the properties of a lower coefficient of friction multi-directional stretch and abrasion resistance as compared to the adherent cellular polymer. These fabrics include, for instance, nylon, LYCRA ® and the like. The fibers are described in "FIBERS" in *Van Nostrand's Scientific Encyclopedia*, 6th Edition, Van Nostrand Reinhold Company of New York published in 1983, pages 1174-1179, which is incorporated herein by reference. Panel 31 having one side with a split texture is attached at a position as shown in FIG. 2 or 3. The attachment is made using an appropriate adhesive such as neoprene contact rubber cement, i.e., (the cellular polymer surfaces are adhered together).

To produce the elastic sleeve, a blank of FIG. 3 is obtained. Panel 31 is cemented to the inner surface of blank 12. The blank-panel is then sewn together using, for instance, a blind stitch 13 and is also cemented. The object of the bonding is to form a seam 13, 14 or 15 which is air tight by bonding edge A to edge B, edge C to edge D and edge E to edge F as shown in FIG. 2 or 3. This action produces completed support sleeve 10 of FIG. 2 where the sleeve assumes a preflexed angle of between about 5° and 45° (preferably between about 10° to 20°).

It is possible within this present invention to combine by sewing two complementary pieces of cellular polymer material having the general shape shown in FIG. 3. The two pieces are joined at the middle to form the "X" shape between edges C-E and edges D-F. Panel 31 (cellular surface) can then be adhered to the inner (cellular) surface of panel 12. The edges C and D then E and F then A and B are sewn together as is described herein to form the elastic sleeve.

Panel 31 may also be adhered in place by any fastening (adhering means) as long as the sleeve remains essentially air tight when in position on the residual limb with the prosthetic device. Panel 31 is shown having a "wavy" pattern to coincide with the standard proximal configuration of a socket of a prosthetic device, however, any similar shape is contemplated so long as the fabric portion of panel extends between about 1 and 2 inches above and below the surface intersection line of the surface flesh of the lower extremity and the external top edge (outer rim) of the socket of the prosthetic device. The purpose of the angle is to reduce constriction through minimizing the "bunching" or "gathering" effect that normally takes place behind the knee. The preformed angle, in conjunction with the material of choice, also serves to enhance suspension by creating vertical force behind the knee at extension. In other words, as the residual leg is lifted and moved forward, as in normal walking, the sleeve provides tension behind the knee to assist in gripping the prosthesis. Overall, the upper circular opening of sleeve 16 is usually larger than the lower circular opening 17. The sleeve 10 has a general truncated conical shape going from larger at the top to smaller at the bottom.

In another embodiment, the sleeve 10 is first created by bonding, using for example, neoprene, rubber contact cement, and stitching, using, for example, a blind stitching. Sleeve 10 is turned inside out and panel 31 is attached permanently using, for example neoprene rubber contact cement, wherein the elastomeric side of panel 31 is adhered to the "inner" surface 12 of sleeve as shown to become an integral part of sleeve.

We attempted to adhere cloth and other fabrics directly to the inner surface 12 of blank 31. The results are listed below:

TABLE 1

| | TEST MATERIALS BONDED TOGETHER | | |
|---|---|---|---|
| Exp | Cellular Polymeric Material | Fabric | Result + Comment |
| 1 | NS1 | Knitted Nylon Fabric | Delaminaton of Fabric Layers |
| 2 | NS1 | Woven Nylon Fabric | Delamination of Fabric Layers |
| 3 | NS1 | Lycra ® Fabric | Delaminaton of Fabric Layers |
| 4 | NS1 | NS1 with a Lycra ® Fabric Facing | Adhered well when stretched in all directions. |

The cellular material and fabric are all bonded using neoprene rubber contact cement.

As can be seen in Table 1, those materials which do not have an elongation in all directions rip apart upon elongation. Only the materials of the type shown in Experiment 4 are suitable to produce the finished sleeve.

One may conclude from Table 1 that any combination of fabric and adhesives that does not essentially match the stretch (elongation) characteristics of the sleeve material will exhibit a high bonding failure rate in the conventional use of this support for a prosthetic device.

FIG. 4 shows an isometric view of sleeve 41 in place with prosthesis device 42. The top of the socket 43 of the prosthesis device is shown in phantom outline—, and the outline corresponding fabric panel 44 of sleeve 41 also shown in phantom outline—.

FIG. 5 is an isometric cutaway view of sleeve 51 with a shin and foot prosthetic device 52, top of the socket 53, and fabric panel 54 (in phantom outline—) of sleeve 51.

FIG. 6 shows an isometric view of a suspension sleeve 61 for a below the elbow amputation of the arm with a below the elbow prosthetic device 62. The top of the socket 63 is shown in phantom outline—, and the outline of the corresponding fabric panel 64 of sleeve 61 is also shown in phantom outline designated—. The arm sleeve is substantially constructed in the same manner as the knee sleeve as is described above. However, the rubber cellular sheet is usually thinner.

FIG. 7 shows an isometric perspective cutaway view of the sleeve 71 with a below the elbow prosthetic device 72. The top of the socket 73 is shown as is the fabric panel 74—.

While some embodiments of the invention have been shown and described herein, it will become apparent to those skilled in the art that various modifications and changes can be made in the elastic tubular support sleeve, the blank to form the sleeve, and the method of making the sleeve and the combination with the prosthetic device without departing from the spirit and scope of the present invention. The present sleeve is an improvement in that the internal panel, having its fabric side in contact with the skin surface of the limb and the top of the socket of the prosthetic device, increases the airtight qualities of the suspension sleeve, reduces the wear of the cellular sheet material, and reduces skin edema. All such modifications and changes coming within the scope of the appended claims are intended to be covered thereby.

We claim:

1. An improved integral elastic tubular suspension sleeve means for holding a prosthetic device under airtight conditions securely on the end of the limb of a human being having a below the knee amputation of a leg or a below the elbow amputation of the arm, which suspension sleeve means comprises:

an elastic substantially tubular suspension sleeve defining a non-linear axis having first and second substantially circular open ends, the first end for receiving and securely gripping the adjacent surface of the amputated limb of the human being and the second substantially circular open end for receiving and gripping securely the outer upper surface of the complementary socket portion of a prosthetic device wherein the first and second open ends of the sleeve have a preflexed angle between about 5° and 45° from a straight tube, said integral elastic sleeve itself formed of:

(i) an X-shaped blank outer laminate of a flexible cellular polymeric material of neoprene rubber having the tradename NS1 having an inner surface with a high coefficient of friction and an outer surface of the sleeve adhered to a surface facing fabric of LYCRA ® having a lower coefficient of friction covering substantially all of the outer surface of the sleeve having adjacent edges which are glued and blind stitched together to form an airtight seam; and (ii) a substantially rectangular inner panel means to reduce deterioration of the interior surface of the sleeve consisting essentially of a smaller sized laminate itself consisting essentially of a cellular polymeric sheet material of neoprene rubber having the tradename NS1 which is adhered to the inner surface of the suspension sleeve having an outer surface fabric of LYCRA ® facing having a lower coefficient of friction, which inner panel is positioned on the interior of the outer laminate to contact the outer intersection line of the outer surface of the prosthetic device and the outer surface of the flesh of the extremity of the human being, wherein the outer laminate and inner laminate are glued together and the outer laminate is formed from an X-shaped blank wherein the top front and the bottom front of the suspension sleeve each have a longitudinal seam formed by tightly joining the complementary inner upper edges and lower inner edges of the X-shaped blank, the middle of the front of the sleeve is seamless, and the top rear to bottom rear of the sleeve has a continuous seam therebetween formed by joining the complementary outer upper and outer lower edges of the X-shaped blank, the overall suspension sleeve produces an essentially air tight seal between the inner surface of the suspension sleeve, the outer surface of the residual limb, and the outer surface of the upper socket of the prosthetic device, and the angle of the knee or elbow is coincident with the angle of the sleeve, wherein the finished sleeve means does not have any external patches of material on its outer surface, and wherein the finished sleeve means minimize the gathering of material that takes place in the back of the knee.

2. A blank comprising flexible elastic components useful in the production of an integral flexible elastic suspension sleeve of claim 1 for ultimate use in combination with an artificial limb prosthesis device, which blank includes:

(j) substantially 'X' shaped laminate of a flexible elastic cellular polymer neoprene rubber sheet material having a high coefficient of friction having an adherent surface facing fabric of LYCRA ® nylon with a low coefficient of friction on one side of the polymeric sheet material; and (jj) a small panel consisting essentially of a laminate of cellular polymeric neoprene rubber and a surface facing fabric having a low coefficient of friction of LYCRA nylon, the non-faced side of the panel is adhered to the nonfaced side of the blank in a substantially central location so that when the sleeve is formed the fabric of the panel is in contact with the intersection line of the upper surface portion of the socket of the prosthetic device and the outer flesh of the residual limb of the human being.

* * * * *